(12) United States Patent
Matsuhama et al.

(10) Patent No.: US 8,302,459 B2
(45) Date of Patent: Nov. 6, 2012

(54) THERMAL CONDUCTIVITY SENSOR

(75) Inventors: Makoto Matsuhama, Kyoto (JP);
Tomoko Seko, Kyoto (JP); Shuji Takada, Kyoto (JP); Hiroshi Mizutani, Kyoto (JP); Takuji Oida, Kyoto (JP); Masahiko Endo, Kyoto (JP); Takuya Ido, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 350 days.

(21) Appl. No.: 12/726,923

(22) Filed: Mar. 18, 2010

(65) Prior Publication Data
US 2010/0242573 A1 Sep. 30, 2010

(30) Foreign Application Priority Data

Mar. 27, 2009 (JP) ................................. 2009-080519
Mar. 27, 2009 (JP) ................................. 2009-080520

(51) Int. Cl.
*G01N 30/66* (2006.01)
*G01N 27/18* (2006.01)

(52) U.S. Cl. ..................... 73/25.03; 73/23.35; 73/25.05; 422/83; 96/106

(58) Field of Classification Search .................. 72/25.03; 73/25.03, 25.05, 23.35; 422/68.1, 70, 83, 422/89; 96/101, 105, 106
See application file for complete search history.

(56) References Cited

U.S. PATENT DOCUMENTS

| | | | | |
|---|---|---|---|---|
| 3,888,110 A * | 6/1975 | Clark | .............................. | 73/23.4 |
| 5,468,962 A * | 11/1995 | Ohishi et al. | .................. | 250/343 |
| 5,831,146 A * | 11/1998 | Newman | ...................... | 73/23.31 |
| 6,928,858 B2 * | 8/2005 | Lin | .............................. | 73/25.03 |
| 2004/0139784 A1 * | 7/2004 | Srinivasan et al. | ........... | 73/23.42 |

FOREIGN PATENT DOCUMENTS

JP 2003042983 2/2003

* cited by examiner

*Primary Examiner* — Hezron E Williams
*Assistant Examiner* — Rodney T Frank
(74) *Attorney, Agent, or Firm* — Alleman Hall McCoy Russell & Tuttle LLP

(57) ABSTRACT

The measurement sensitivity is improved by suppressing the surrounding temperature influence as much as possible, while realizing scale reduction, and by enlarging the detection signal, while reducing the production errors in enclosing a reference gas. Provided is a thermal conductivity sensor that detects thermal conductivity of a sample gas by using a Wheatstone Bridge circuit constructed in such a manner that measurement resistors that are brought into contact with the sample gas are disposed on a first side, and reference resistors that are brought into contact with a reference gas are disposed on a second side, and comparing the potential difference between connection points of the reference resistors and the measurement resistors. The measurement resistors disposed on the first side are assembled in one measurement space, and the reference resistors disposed on the second side are assembled in one reference space.

2 Claims, 6 Drawing Sheets

THERMAL CONDUCTIVITY SENSOR

BACKGROUND OF THE INVENTION

1. Field of the Invention

The present invention relates to a thermal conductivity sensor that detects the thermal conductivity of a sample gas by using a Wheatstone Bridge circuit and measures the concentration of a predetermined component in the sample gas based on the thermal conductivity.

2. Description of the Related Art

Conventionally, a thermal conductivity sensor of this kind is constructed in such a manner that one measurement resistor is assembled in a measurement cell; one reference resistor is assembled in a reference cell; and other resistors are disposed outside of the cells as external resistors, constituting a Wheatstone Bridge circuit, as described in Japanese Patent Application Laid-open (JP-A) No. 2003-42983.

However, since the disposal temperature and the temperature coefficient are different between the external resistors, and the measurement resistor and the reference resistor, the temperature influence received from the outside is different between the external resistors, and the measurement resistor and the reference resistor, thereby making it difficult to obtain correct measurement results.

For this reason, it is possible to consider providing a temperature correction circuit for correcting at least the temperature influence that the external resistors receive. However, the temperature influence that the external resistors receive may be different product by product due to the variation in the temperature coefficient of the external resistors, so that a correction coefficient of the temperature correction circuit must be set product by product, and the setting thereof is cumbersome, thereby causing an increase in costs.

Further, by electric signals from one measurement resistor and one reference resistor alone, the signal amount will be small, to aggravating the signal-to-noise (SN) ratio and, as a result thereof, the measurement in a low-concentration range is difficult.

There is also a thermal conductivity sensor based on the above-described type of sensor, in which one in which four cells (two measurement cells and two reference cells) are used, and a measurement resistor or a reference resistor is assembled in each cell; however, this raises problems in that the production costs will increase and scale reduction is difficult. Also, a reference gas such as an $N_2$ gas must be enclosed in the two reference cells, thereby raising a problem that production errors, such as inevitable variation in the enclosure, lead to measurement errors.

SUMMARY OF THE INVENTION

Therefore, the present invention has been made for simultaneously solving the aforementioned problems, and a principal object thereof is to improve the measurement sensitivity by enlarging the detection signal while enabling scale reduction, eliminating the need for external resistors, and reducing the production errors in enclosing a reference gas.

That is, the thermal conductivity sensor according to the present invention is a thermal conductivity sensor that detects a thermal conductivity of a sample gas by using a Wheatstone Bridge circuit constructed in such a manner that measurement resistors that are brought into contact with the sample gas are disposed on a first side, and reference resistors that are brought into contact with a reference gas are disposed on a second side, and comparing the potential difference between connection points of the reference resistors and the measurement resistors, wherein the measurement resistors disposed on the first side are assembled in one measurement space in which the sample gas is housed, and the reference resistors disposed on the second side are assembled in one reference space in which the reference gas is housed.

With such an apparatus, since the measurement resistors disposed on a side are assembled in one measurement space and the reference resistors disposed on a side are assembled in one reference space, the thermal conductivity sensor can be reduced in scale. Also, the Wheatstone Bridge circuit is constructed with two measurement resistors and two reference resistors, thereby eliminating the need for external resistors for constituting the Wheatstone Bridge circuit. Further, since only one reference space is provided, the production errors in enclosing a reference gas can be reduced. Also, the number of components can be reduced, and the apparatus can contribute to cost reduction. In addition, the detection signal can be doubled as compared with a case in which one measurement space and one reference space are simply provided and one measurement resistor and one reference resistor are provided in the spaces, so that the measurement sensitivity can be improved.

In order to let the temperature influence received by the measurement resistors be as close as possible and to let the temperature influence received by the reference resistors be as close as possible, so as to enable measurement at high precision, and also to achieve scale reduction of the sensor, it is desirable that the measurement resistors disposed on the first side are made of two thin film resistor bodies formed on one substrate surface, and that the reference resistors disposed on the second side are made of two thin film resistor bodies formed on one substrate surface.

In order to enhance the sensitivity as a thermal conductivity sensor, it is desirable to increase the amount of applied electric current as much as possible; however, in accordance therewith, the sensor temperature rises. In measuring a combustible gas with use of the present sensor according to an explosion protection standard, there is an upper limit on the sensor temperature due to the explosion protection standard. At this time, in order to obtain a uniform temperature distribution within a range that does not exceed the upper limit, it is desirable that at least the thin film resistor bodies, constituting the aforementioned measurement resistors, have a pattern formation part formed in a pattern on the substrate surface, and the pattern formation part has a pattern shape having a density that is highest at peripheral parts and gradually decreases toward a central part, whereby a temperature of a neighborhood of the pattern formation part can be raised to a generally uniform temperature when the pattern formation part is energized.

According to the present invention constructed in this manner, the measurement sensitivity can be improved by enlarging the detection signal while eliminating the need for external resistors, enabling scale reduction, and reducing the production errors in enclosing a reference gas.

DESCRIPTION OF THE PREFERRED EMBODIMENTS

Hereafter, one embodiment of a thermal conductivity sensor according to the present invention will be described with reference to the drawings.

A thermal conductivity sensor 100 according to the present embodiment detects the thermal conductivity of a sample gas containing a combustible and/or corrosive component and measures the concentration of a predetermined component in the sample gas based on the thermal conductivity. Here, the combustible and/or corrosive component may be, for example, water ($H_2O$), an oxygen ($O_2$) gas, a sulfur oxide ($SO_x$) gas, a nitrogen oxide ($NO_x$) gas, a hydrochloric acid (HCl) gas, an ammonia ($NH_3$) gas, a hydrogen sulfide ($H_2S$) gas, or a hydrogen ($H_2$) gas.

Figure 1:
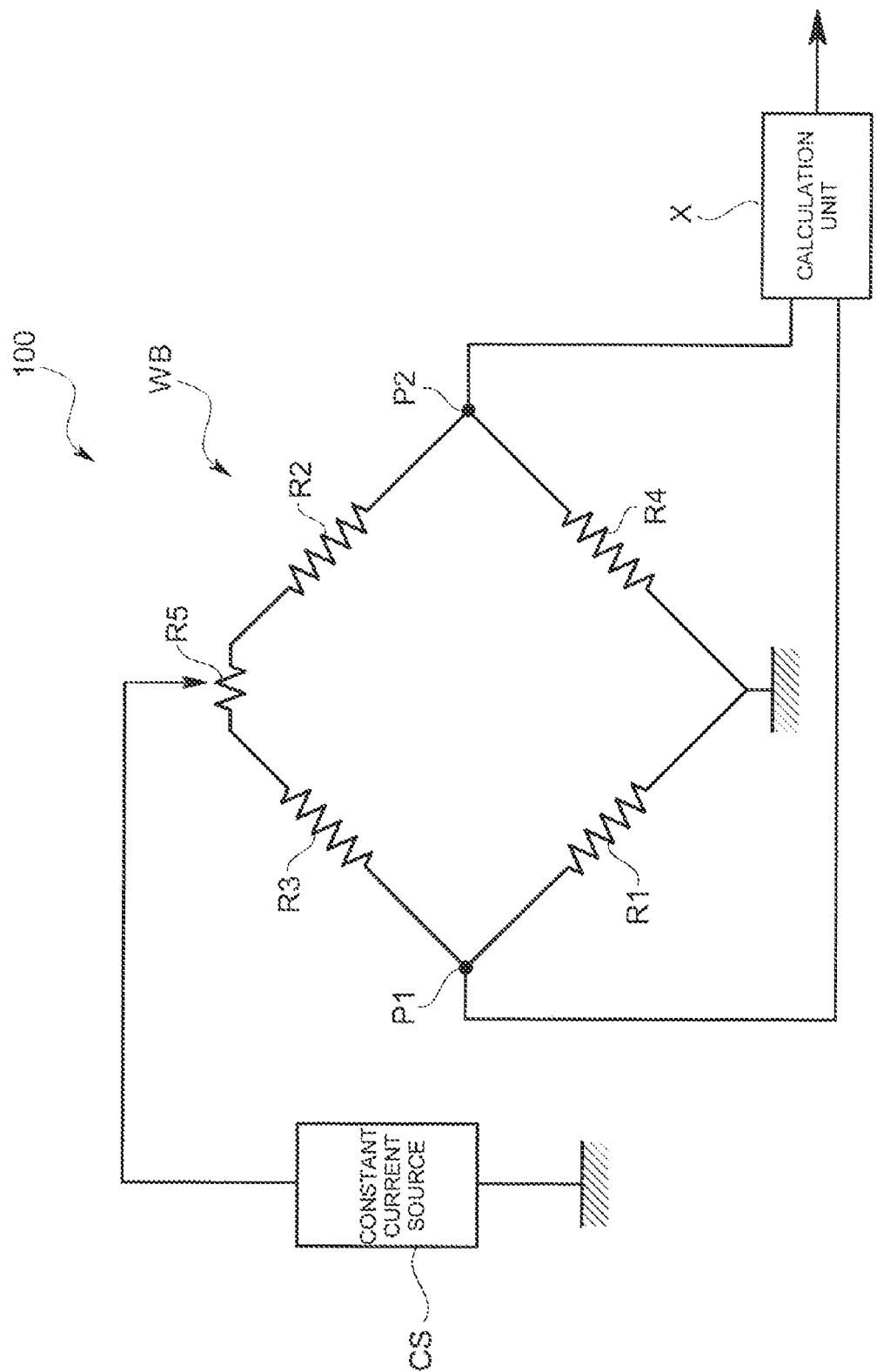
FIG. 1 is a drawing showing a measurement circuit of a thermal conductivity sensor according to one embodiment of the present invention.

First, a measurement circuit of the thermal conductivity sensor 100 will be described with reference to FIG. 1.

This measurement circuit is constructed with two measurement resistors R1 and R2 that are disposed to be in contact with a sample gas and two reference resistors R3 and R4 that are disposed to be in contact with a reference gas. Specifically, the measurement circuit is constructed by using a Wheatstone Bridge circuit WB that is constructed by parallel connection of two series circuit portions formed by series connection of one of the measurement resistors R1 or R2 and one of the reference resistors R3 or R4.

At this time, the two series circuit portions are connected in parallel so that the measurement resistors R1 and R2 of each series circuit portion may be positioned on sides opposite to each other and so that the reference resistors R3 and R4 of each series circuit portion may be positioned on sides opposite to each other. Further, a constant current source CS is connected between connection points of each series circuit portion. Here, at one of the connection points of each series circuit portion, a variable resistor R5 for offset adjustment is provided. In such a construction, a calculation unit X detects the potential of the connection points P1 and P2 of the measurement resistors R1 and R2 and the reference resistors R3 and R4 in each series circuit portion, and obtains the potential difference between these connection points P1 and P2 as a detection signal, whereby the concentration of a predetermined component in the sample gas is calculated. Here, at least the thermal conductivity sensor 100, the constant current source CS, and the calculation unit X constitute a gas analyzing apparatus.

Next, the equipment construction of the thermal conductivity sensor 100 will be described.

The thermal conductivity sensor 100 of the present embodiment includes the aforementioned Wheatstone Bridge circuit WB in the inside, and is provided with a casing (not illustrated) having a pressure-resistant and explosion-proof structure in which an inlet for introducing a sample gas to the inside and an outlet for discharging the sample gas to the outside are formed, and an internal block body 2 (see FIG. 2) having a pressure-resistant and explosion-proof structure that is disposed in the casing and is in communication with the aforementioned inlet and outlet.

Figure 2:
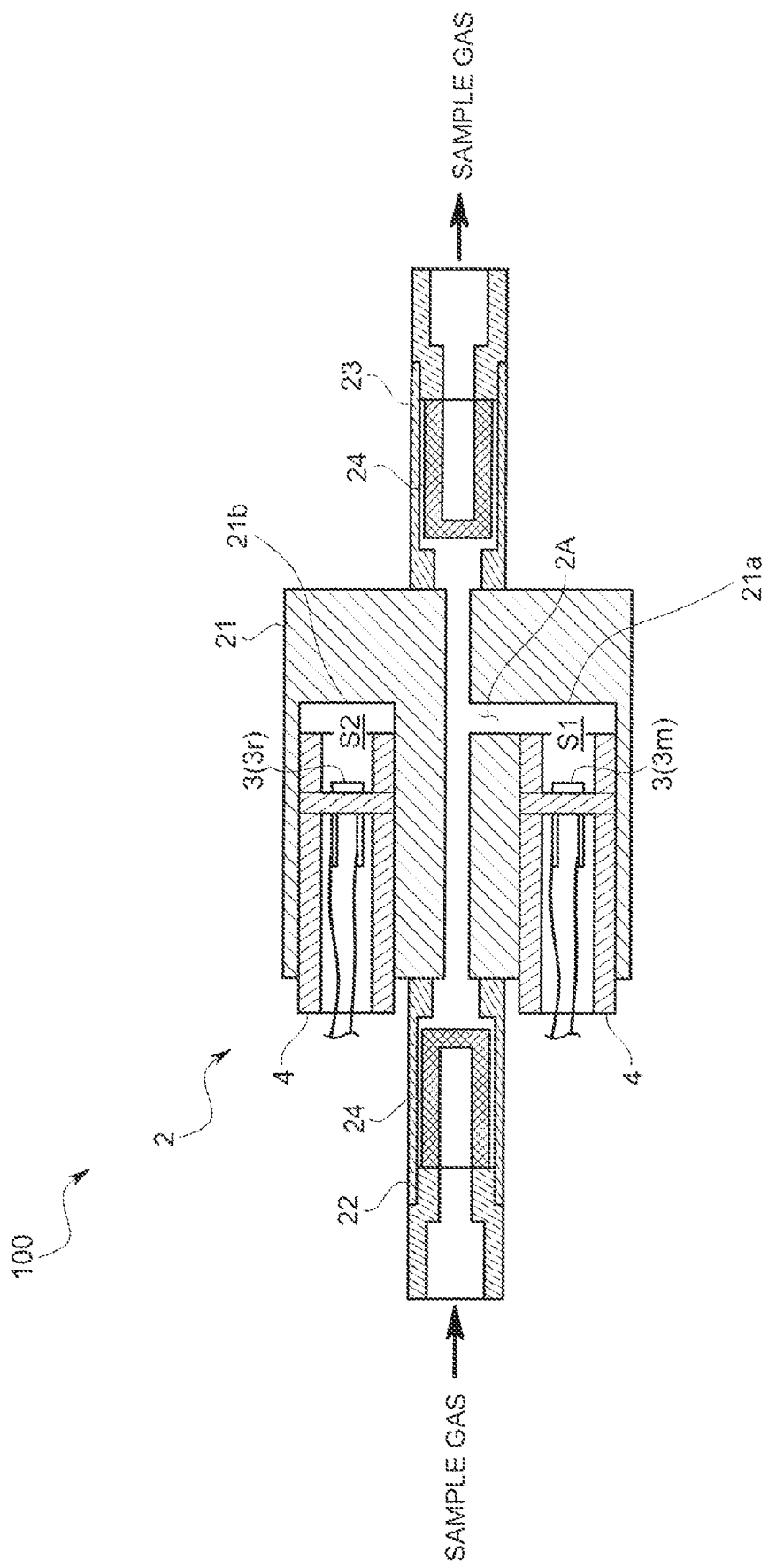
FIG. 2 is a cross-sectional view showing an internal block body of the thermal conductivity sensor according to the embodiment.

Further, as shown in FIG. 2, the internal block body 2 is provided with a block main body 21 in which an internal flow passageway 2A is formed, an introduction pipe connection part 22 disposed in this block main body 21 to be in communication with the internal flow passageway 2A and connected to the inlet via a pipe, and a discharge pipe connection part 23 disposed in this block main body 21 to be in communication with the internal flow passageway 2A and connected to the outlet via a pipe.

Here, in the introduction pipe connection part 22 and in the discharge pipe connection part 23, respectively, a sintered metal element 24 is disposed to partition the flow passageway within the connection part into the block main body 21 side (ignition source side) and the pipe side. Specifically, the sintered metal element has a tubular form having a bottom, and is disposed along the flow passageway so that the bottom part thereof will be directed towards the block main body 21 side.

By providing the sintered metal element 24 in each of the connection parts 22 and 23, when a flame is generated within the block main body 21, the flame is prevented from reaching the outside of the connection parts 22 and 23. Therefore, the construction can be simplified and the production costs can be reduced without the need for making the construction of the pipes and the construction of the joints for connecting the pipes to the connection parts 22 and 23 be an exclusive-use construction, based on the Recommended practices for explosion-protected electrical installations in general industries (publisher: independent administrative organization, National Institute of Occupational Safety and Health, Japan).

The block main body 21 is formed from an anti-corrosive material such as stainless steel, and a measurement space S1, in which a sensor substrate 3, having the measurement resistors R1 and R2 formed therein (hereafter referred to as a "measurement substrate 3m" when specifically distinguished) is disposed and is formed on the internal flow passageway 2A of the block main body 21.

Specifically, by air-tight insertion of a sensor holder 4 for holding the measurement substrate 3m into a recess 21a that forms a part of the internal flow passageway 2A, the measurement space S1 is formed by the sensor holder 4 and the recess 21a, and the measurement substrate 3m is disposed within the measurement space S1.

Also, a reference space S2, in which a sensor substrate 3 having the reference resistors R3 and R4 formed therein (hereafter referred to as a "reference substrate 3r" when specifically distinguished) is disposed and is formed in the block main body 21. A reference gas is enclosed in this reference space S2, and the reference space S2 is disposed independently from the internal flow passageway 2A.

Specifically, by air-tight insertion of a sensor holder 4 for holding the reference substrate 3r into a recess 21b formed in the block main body 21, the reference space S2 is formed by the sensor holder 4 and the recess 21b, and the reference substrate 3r is disposed within the reference space S2. Here, the sensor holder 4 for holding the reference substrate 3r and the sensor holder 4 for holding the measurement substrate 3m are made to have the same construction.

Figure 3:
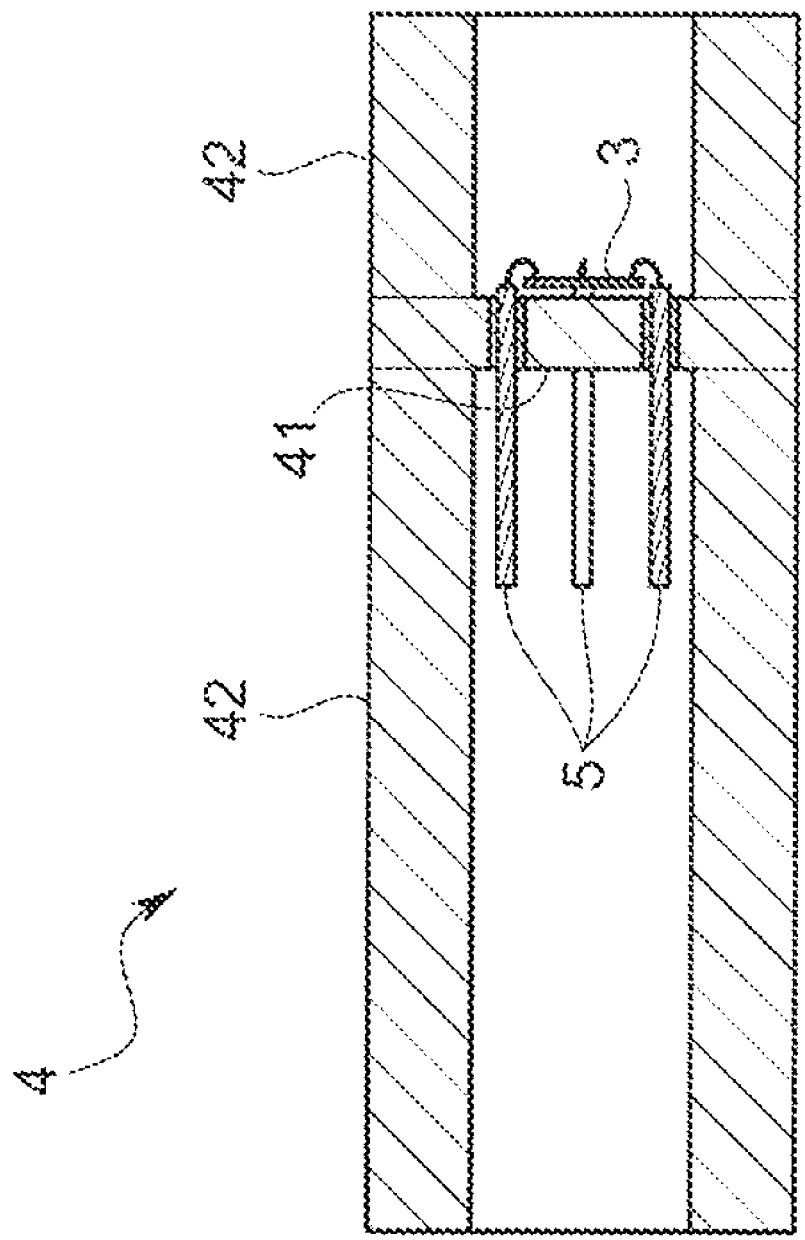
FIG. 3 is a cross-sectional view showing the internal block body of the embodiment.

This sensor holder 4 is formed from an anti-corrosive material such as stainless steel, and has a generally cylindrical shape. Further, as shown in FIG. 3, this sensor holder 4 includes a base body 41 having a generally disk shape to which the sensor substrate 3 and a lead pin 5 electrically connected to the sensor substrate 3 are fixed, and a holder main body 42 that is fixed to sandwich the base body 41 from both sides. Here, the base body 41 and the holder main body 42 are connected by whole-circumference laser welding.

Now, the thermal conductivity sensor 100 of the present embodiment is constructed in such a manner that the measurement resistors R1 and R2 disposed on a first opposite side constituting the Wheatstone Bridge circuit WB are disposed in one measurement space S1, and the reference resistors R3 and R4 disposed on a second opposite side are disposed in one reference space S2. In other words, the measurement resistors R1 and R2 are disposed on one measurement substrate 3m; the reference resistors R3 and R4 are disposed on one reference substrate 3r; the measurement substrate 3m is disposed in one measurement space S1; and the reference substrate 3r is disposed in one reference space S2. Here, one measurement space S1 is a space formed by one measurement cell, and is not one formed in such a manner that two measurement cells are brought into communication with each other by a pipe or the like. In the present embodiment, one sensor holder 4 and the block main body 21 constitute one measurement cell. Also, one reference space S2 is a space formed by one reference cell, and is not one formed in such a manner that two reference cells are brought into communication with each other by a pipe or the like. In the present embodiment, one sensor holder 4 and the block main body 21 constitute one reference cell.

Here, the measurement substrate 3m and the reference substrate 3r will be described.

Figure 4:
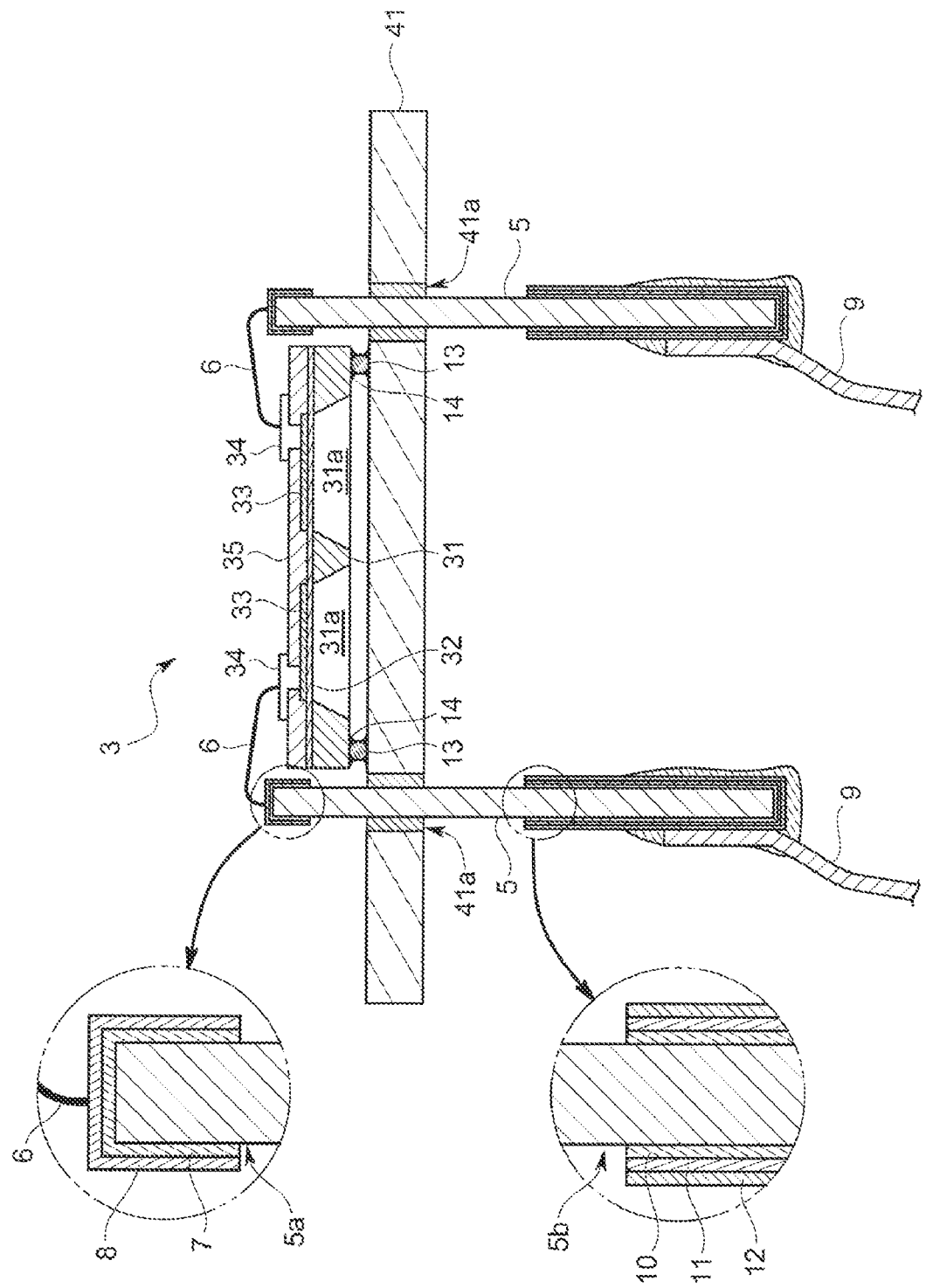
FIG. 4 is a schematic cross-sectional view of a base body, a sensor substrate, and a lead pin of the embodiment.

As shown in FIG. 4, the measurement substrate 3m includes a silicon substrate 31 provided with hollow portions 31a having a rectangular shape in a plan view, a resistor body holding film 32 (constructed, for example, with an $SiO_2$ film and an $Si_3N_4$ film formed on the $SiO_2$ film) having a diaphragm structure disposed on this silicon substrate 31 to intervene the hollow portions 31a, thin film resistor bodies 33 formed on this resistor body holding film 32 and made of platinum, and a pad portion 34 made of gold that will be a wiring connection portion in contact with each end of the thin film resistor bodies 33. Here, the top of the thin film resistor bodies 33 and the resistor body holding film 32 is partly covered with a surface protective film 35 such as a TEOS-$SiO_2$ film. Also, the reference substrate 3r has the same construction as the measurement substrate 3m.

Specifically, the silicon substrate 31 constituting the measurement substrate 3m and the silicon substrate 31 constituting the reference substrate 3r have the same shape, and both have a rectangular shape in a plan view in the present embodiment. Also the pattern of the thin film resistor bodies 33 constituting the measurement substrate 3m and the pattern of the thin film resistor bodies 33 constituting the reference resistors R3 and R4 are formed to have the same pattern, and are made to have the same resistance value. The other films have the same construction. By making the measurement substrate 3m and the reference substrate 3r have an identical construction in this manner, temperature characteristics of the measurement substrate 3m and the reference substrate 3r are made identical.

Also, the measurement resistors R1 and R2 arranged on a first opposite side of the Wheatstone Bridge circuit are made of the two thin film resistor bodies 33 formed in a pattern on one silicon substrate 31, and the reference resistors R3 and R4 arranged on a second opposite side are made of the two thin film resistor bodies 33 formed in a pattern on one silicon substrate 31.

Figure 5:
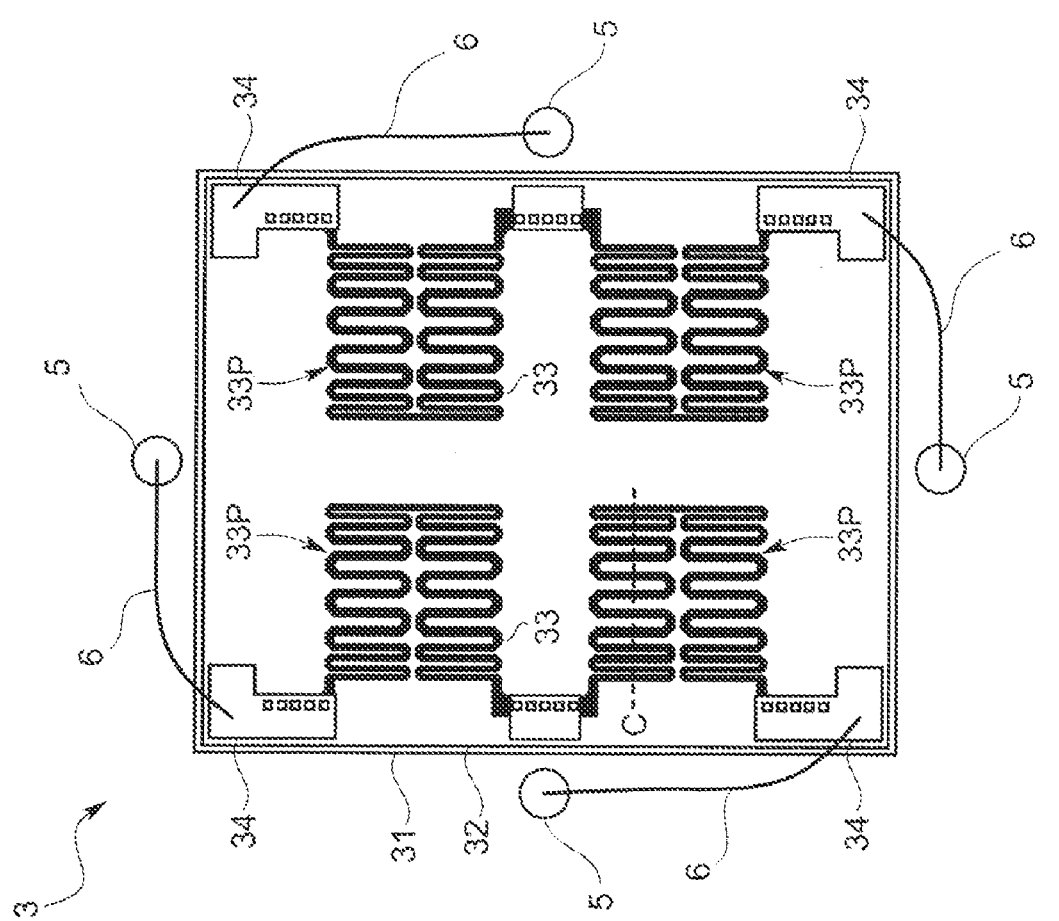
FIG. 5 is a plan view showing the sensor substrate of the embodiment.

Here, as a representative, the pattern of the thin film resistor bodies 33 constituting the measurement resistors R1 and R2 will be described with reference to FIG. 5.

The thin film resistor bodies 33 constituting the measurement resistors R1 and R2 are formed independently for each region obtained by equally dividing the silicon substrate 31 surface into two. Also, the thin film resistor body 33 formed in each region is formed symmetrically relative to the bisecting line.

Specifically, each thin film resistor body 33 has two pattern formation parts 33P that are formed in a pattern on the silicon substrate 31 (specifically, the resistor body holding film 32) surface, and each pattern formation part 33P has a pattern shape having a density that is highest at peripheral parts and gradually decreases toward a central part, whereby a temperature of a neighborhood of the pattern formation part 33P can be raised to a generally uniform temperature when the pattern formation part 33P is energized.

To describe in a greater detail, the pattern formation part 33P is formed in a double-zigzag pattern shape in which the line width of the thin film resistor body 33 and the line interval (pitch) of the thin film resistor body 33 both attain the minimum value at both end parts in one direction (for example, in a right-and-left direction), and the line width of the thin film resistor body 33 and the line interval (pitch) of the thin film resistor body 33 gradually increase according as they come closer to the central part.

Here, in order to enhance the sensor sensitivity in the thermal conductivity sensor 100 of the present embodiment, it is desirable to raise the temperature of the thin film resistor bodies 33 (the measurement resistors R1 and R2 and the reference resistors R3 and R4) as much as possible. However, since the upper limit value of the temperature of the thin film resistor bodies 33 is limited by the explosion protection standard, the temperature preferably has a broad temperature distribution rather than a temperature distribution having a peak.

Figure 6:
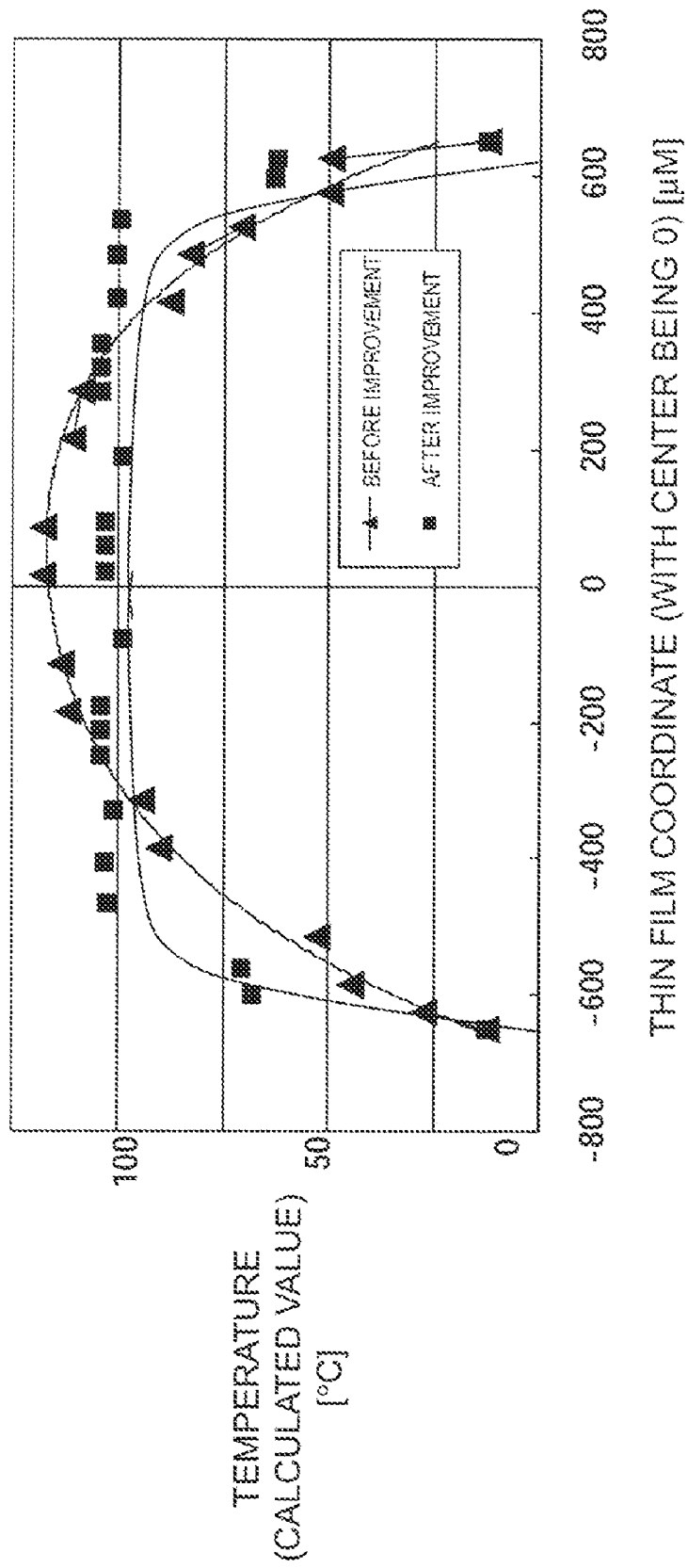
FIG. 6 is a simulation result showing a temperature distribution of a thin film resistor body of the embodiment.

From this viewpoint, a simulation result of the temperature distribution of the thin film resistor bodies 33 of the present embodiment is shown in FIG. 6. The temperature (Y-axis) shown in FIG. 6 shows a temperature along the line C in FIG. 5. Also, the term "after improvement" in FIG. 6 shows a temperature distribution in the thin film resistor bodies 33 of the present embodiment, whereas the term "before improvement" shows a temperature distribution in the thin film resistor bodies 33 of a comparative example in which the pattern of the pattern formation part of the thin film resistor bodies is formed in a double zigzag pattern such that the line width of the thin film resistor bodies and the line interval of the thin film resistor bodies are made identical both at the two end parts and at the central part so that the density at the peripheral parts and the density at the central part will be equal.

As will be understood from FIG. 6, the temperature "before improvement" has a peak at the central part, and the peak is limited by the explosion protection standard temperature (specifically, 130° C.), so that the temperature of the other parts cannot be raised beyond that. On the other hand, it will be understood that the temperature "after improvement" forms a uniform temperature distribution below or equal to the explosion protection standard temperature (specifically, 130° C.).

<Wiring Structure of Sensor Substrate 3>

In a conventional gas sensor, a sensor substrate in which circuit elements such as measurement resistors, constituting a Wheatstone Bridge circuit, are formed is disposed in a measurement space. On this sensor substrate, a pad portion made of gold or platinum which will be a wiring connection part of the circuit elements is formed. Further, one end part is wire-bonded to a lead pin disposed in the measurement space.

Here, in the event that the sample gas contains an acidic or alkaline corrosive component, the lead pin must have an anti-corrosion property, so that in a conventional case, iron (Fe) having a small anti-corrosion property, for example, is used after being plated with copper (Cu), then being plated with nickel (Ni), and further being plated with gold (Au).

However, when there is a pinhole (fine hole) in the plating, the corrosive component penetrates through the fine hole, whereby the lead pin will be corroded to invite poor conduction, thereby raising problems such as generation of errors in the detection signal.

At this time, it may be possible to increase the thickness of the plating in order to eliminate the pinholes; however, increasing the thickness of the plating naturally raises a problem of increase in costs.

The gas sensor according to the present invention has been made in order to solve the aforementioned problems simultaneously, and an object thereof is to enable increase in the lifetime by improving the anti-corrosion property and to improve the electric connection property between the pad portion of the sensor substrate and the lead pin.

That is, the gas sensor according to the present invention includes a sensor substrate disposed in a measurement space, having circuit elements formed thereon for detecting a sample gas, and having a pad portion made of gold or platinum that will be a wiring connection part of the circuit elements, a lead pin made of a nickel alloy whose one end is disposed in the measurement space to be electrically connected to the pad portion and whose other end is disposed outside of the measurement space, and a connection body made of gold or platinum that establishes electric connection between the pad portion and one end part of the lead pin, wherein a first layer made of chromium, tungsten, or titanium and a second layer made of gold or platinum and disposed on the first layer are formed at one end part of the lead pin.

With such an apparatus, since the lead pin is made of a nickel alloy, the lead pin can be made to have an anti-corrosion property, thereby preventing poor conduction to solve problems such as generation of errors in the detection signal and also enabling increase in the lifetime. Further, by forming the first layer made of chromium or the like and the second layer made of gold or the like at one end part of the lead pin and connecting the connection body to the second layer, the electric connection property between the connection body and the lead pin can be improved.

Also, in order to improve the electric connection property between an external conduction wire and the lead pin, it is desirable that a first layer made of chromium, tungsten, or titanium and a second layer made of nickel and disposed on the first layer are formed at the other end part of the lead pin, and that the external conduction wire is connected to the second layer.

In order to alleviate the stress generated in the sensor substrate caused by the difference between the thermal expansion coefficient of the member that holds the sensor substrate and the thermal expansion coefficient of the sensor substrate so as to prevent damage to the sensor substrate in a suitable manner, it is preferable that the sensor is provided with a base body that holds the sensor substrate within the measurement space, and an intermediate body having a thermal expansion coefficient lying between the thermal expansion coefficient of the base body and the thermal expansion coefficient of the sensor substrate is preferably allowed to intervene between the base body and the sensor substrate.

Specifically, as shown in FIG. 4, the sensor holder 4 is provided with an anti-corrosive lead pin 5 whose first end part 5a is disposed in the spaces S1 and S2 to be electrically connected to the pad portion 34 and whose second end part 5b is disposed outside of the spaces S1 and S2. An insertion hole 41a into which the lead pin 5 is inserted is formed in the base body 41 of the sensor holder 4, and the lead pin 5 is air-tightly fixed by glass sealing in a state in which the lead pin 5 is inserted into the insertion hole 41a.

The lead pin 5 is made of a material exhibiting an anti-corrosion property to a corrosive gas, and specifically is a rod-shaped member made of a nickel alloy. Here, the nickel alloy in the present embodiment is an alloy containing nickel (Ni) as a major component and containing cobalt (Co), chromium (Cr), molybdenum (Mo), tungsten (W), iron (Fe), silicon (Si), manganese (Mn), carbon (C), or the like.

Also, the first end part 5a (measurement space S1 side end part) of the lead pin 5 and the pad portion 34 of the measurement substrate 3 are electrically connected by a connection body 6. This connection body 6 is connected to the pad portion 34 and the first end part 5a of the lead pin 5 by wire bonding, and is a gold wire in the present embodiment.

Then, in order to connect the nickel alloy and the gold wire 6 electrically by wire bonding and to improve the anti-corrosion property, a first layer 7 (Cr layer) made of chromium (Cr) and a second layer 8 (Au layer), made of gold (Au) and disposed on the first layer 7, are formed at the first end part 5a of the lead pin 5, as shown in the partially enlarged view at the upper part of FIG. 4. Further, the Au wire 6 is connected by supersonic welding. Here, the supersonic welding presses the gold wire 6 onto the lead pin 5 with a jig, and scrapes the gold wire 6 by supersonic vibration of about several ten KHz, and performs welding by the friction heat generated at that time and the pressing force.

In the present embodiment, the film thickness of the Cr layer 7 formed at the first end part 5a of the lead pin 5 is, for example, 100 to 500 Å, and the film thickness of the Au layer 8 is, for example, 2000 Å or more.

Although it is difficult to form the Au layer 8 on a nickel alloy, by forming the Cr layer 7 as described above and thereafter forming the Au layer 8 on the Cr layer 7, the Au layer 8 can be formed at the measurement space S1 side end part (inner lead side) of the lead pin 5. Also, since the Cr layer 7 is liable to be oxidized, even if a pinhole (fine hole) is generated in the Au layer 8, the Cr layer 7 exposed to the outside by the pinhole forms an oxide film, whereby progress of the oxidation can be suppressed to improve the anti-corrosion property.

Also, in order to improve the connection property between the nickel alloy and an external conduction wire 9 (for example, a lead wire made of copper (Cu)), a first layer 10 (Cr layer) made of chromium (Cr), a second layer 11 (Ni layer) made of nickel (Ni) and disposed on the first layer 10, and a third layer 12 (Au layer) made of gold (Au) and disposed on the second layer 11 are formed at the second end part 5b of the lead pin 5 (the end part opposite to the measurement space S1), as shown in the partially enlarged view at the lower part of FIG. 4.

In the present embodiment, the film thickness of the Cr layer 10 formed at the second end part 5b of the lead pin 5 is, for example, 100 to 500 Å; the film thickness of the Ni layer 11 is, for example, 8000 Å or more; and the film thickness of the Au layer 12 is, for example, 500 Å or less.

Although it is difficult to form the Ni layer 11 on a nickel alloy, by forming the Cr layer 10 as described above and thereafter forming the Ni layer 11 on the Cr layer 10, the Ni layer 11 can be formed at the second end part 5b of the lead pin 5 (the outer lead side). Then, by joining the external conduction wire 9 to the Ni layer 11 by soldering, the external conduction wire 9 and the nickel alloy (lead pin 5) can be electrically connected. Also since the Au layer 12 is formed on the Ni layer 11, oxidation of the Ni layer 11 can be prevented. Here, in the soldering of the external conduction wire 9, the Au layer 12 is molten, whereby the external conduction wire 9 and the Ni layer 11 will be connected.

<Film Formation Method and Others>

Next, one example of a method of forming a film of each layer to the lead pin 5 will be described.

First, the lead pin 5 is inserted into the insertion hole 41a disposed in the base body 41 of the sensor holder 4, and the lead pin 5 is fixed relative to the base body 41 by glass sealing. Thereafter, a mask substrate having a through-hole corresponding to the insertion hole 41a of the base body 41 is superposed from the measurement space S1 side of the base body 41 so that the lead pin 5 will be inserted into the insertion hole 41a. At this time, the part exposed from the mask substrate will be a part that will be formed as a film. In this state, films of the Cr layer 7 and the Au layer 8 are formed in this order on the exposed parts from the mask substrate by a thin film production technique such as the sputtering method, the vacuum vapor deposition method, or the CVD method. Thereafter, by removing the mask substrate, the Cr layer/Au layer is formed at the first end part 5a of the lead pin 5.

Also, a mask substrate having a through-hole corresponding to the insertion hole 41a of the base body 41 is superposed from the opposite side of the measurement space S1 of the base body 41 so that the lead pin 5 will be inserted into the insertion hole 41a. At this time, the part exposed from the mask substrate will be a part that will be formed as a film. In this state, films of the Cr layer 10, the Ni layer 11, and the Au layer 12 are formed in this order on the exposed part from the mask substrate by the aforementioned thin film production technique. Thereafter, by removing the mask substrate, the Cr layer/Ni layer/Au layer is formed at the second end part 5b of the lead pin 5.

After the films are formed at both the end parts 5a and 5b of the lead pin 5, the gold wire 6 for electrically connecting to the sensor substrate 3 is joined by supersonic joining to the first end part 5a of the lead pin 5. On the other end, the external conduction wire 9 is joined by soldering to the second end part 5b of the lead pin 5. Thereafter, the holder main body 42 is welded by laser to the base body 41. By this process, the sensor substrate 3 and the lead pin 5 are electrically connected, and a sensor unit is formed in which they are fixed to the sensor holder 4.

Next, results of an anti-corrosion test of the sensor holder 4 using the lead pin 5 constructed in this manner will be described. The gas used in this anti-corrosion test is a gas containing 50% or more of nitrogen monoxide (NO) or nitrogen dioxide ($NO_2$). Also, for comparison, a similar test was carried out on a thermal conductivity sensor (hereafter referred to as a conventional product 1) in which the base body and the lead pin are made of iron and they are subjected to gold plating and on a thermal conductivity sensor (hereafter referred to as a conventional product 2) in which the base body and the lead pin are made of iron and they are subjected to gold plating and coated with an epoxy-based resin.

In the conventional product 1, the base body and the lead pin were corroded in one or two days. In the conventional product 2, the base body and the lead pin were corroded in about 20 days. On the other hand, in the thermal conductivity sensor 100 of the present embodiment, the base body 41 and the lead pin 5 were not corroded even after about 250 days had passed.

<Stress Alleviation Structure>

Also, in the thermal conductivity sensor 100 according to the present embodiment, an intermediate body 13 having a thermal expansion coefficient lying between the thermal expansion coefficient of the base body 41 and the thermal expansion coefficient of the sensor substrate 3 is allowed to intervene between the base body 41 of the sensor holder 4 and the sensor substrate 3. Further, the base body 41 and the intermediate body 13 are bonded, and the intermediate body 13 and the sensor substrate 3 are bonded by an adhesive agent 14. Here, as the adhesive agent 14, it is possible to use, for example, an epoxy-based adhesive agent.

Since the base body 41 of the present embodiment is made of stainless steel, the thermal expansion coefficient thereof is about $16 \times 10^{-6}$ [/° C.], and the sensor substrate 3 is one using the silicon substrate 31, the thermal expansion coefficient thereof is about $2.4 \times 10^{-6}$ [/° C.], it is preferable that the thermal expansion coefficient of the intermediate body 13 is one lying therebetween. In particular, for the intermediate body 13 of the present embodiment, it is conceivable to use zirconia ($ZrO_2$) having a high melting point, having good chemical stability, and having a small thermal conductivity (the thermal expansion coefficient is about $10 \times 10^{-6}$ [/° C.]) or alumina ($Al_2O_3$) being excellent in ordinary temperature strength, anti-corrosion property, and electric insulation property (the thermal expansion coefficient is about $8.1 \times 10^{-6}$ [/° C.]); however, it is particularly preferable to use zirconia widely applicable to corrosive gases.

Since the intermediate body 13 such as this is allowed to intervene, the stress generated in the sensor substrate 3 by the base body 41 can be alleviated, thereby solving a problem of generation of warpage, breakage, or the like in the resistor body holding film 32 or the like.

Also, the intermediate body 13 has, for example, a generally spherical shape having a diameter of 400 μm or more. By this, in the case of bonding the base part 41 and the sensor substrate 3 by allowing the intermediate body 13 to intervene, the contact area between the adhesive agent 14 and the intermediate body 13 can be increased, so that the sensor substrate 3 can be firmly fixed to the base part 41. That is, occurrence of adhesive failure by the stress generated by the difference in thermal expansion can be prevented. Also, by the surface tension of the adhesive agent 14 applied onto the intermediate body 13, the sensor substrate 3 can be positioned relative to the intermediate body 13.

Finally, a combination of the base body 41 and the lead pin 5 will be mentioned.

According to conventional construction, the base body and the lead pin are made of iron; gold plating is carried out in order to facilitate the bonding of wires; and glass is used for glass sealing of the base body and the lead pin. Since the thermal expansion coefficient of iron is about $10 \times 10^{-6}$ [/° C.] and the thermal expansion coefficient of glass is about $9.5 \times 10^{-6}$ [/° C.], the base body and the lead pin undergo similar thermal expansion, so that decrease in the air-tightness of the glass sealing caused by temperature variation will not occur. However, as described above, when there are pinholes (fine holes) in the gold plating, a corrosive component penetrates through the fine holes, thereby raising a problem that the lead pin made of iron will be corroded.

Here, in order to allow the sensor to have an anti-corrosion property, it is conceivable to construct the base body and the lead pin to be made of stainless steel.

However, even when use of glass for glass sealing of the base body made of stainless steel and the lead pin made of stainless steel is tried, there arises a problem in that a gap is liable to be generated between the lead pin and the glass. For example, due to the difference in temperature at the time of melting and enclosing the glass and at the time of cooling and solidifying the glass in the production, since the thermal expansion coefficient of stainless steel is about $16 \times 10^{-6}$ [/° C.] and the thermal expansion coefficient of glass is about $9.5 \times 10^{-6}$ [/° C.] a gap is liable to be generated between the lead pin and the glass. Therefore, it is not possible to use stainless steel in the lead pin because of the problem regarding air-tightness.

Therefore, in the thermal conductivity sensor 100 of the present embodiment, a nickel alloy (having a thermal expansion coefficient of about $10.0 \times 10^{-6}$ [/° C.]) is used in the lead pin 5 and stainless steel is used in the base body 41, and these are glass-sealed. As a result thereof, the base body 41 and the lead pin 5 can be allowed to have an anti-corrosion property. Also, since the thermal expansion coefficients of glass and nickel are close to each other, the glass and the lead pin 5 undergo similar thermal shrinkage at the time of cooling and solidifying the glass, so that the gap is hardly generated between the glass and the lead pin 5. Also, by using stainless steel having a large thermal expansion coefficient in the base body 41, an even higher air-tightness can be ensured at the time of thermal shrinkage thereof.

Effects of the Present Embodiment

With the thermal conductivity sensor 100 according to the present embodiment constructed as described above, the measurement resistors R1 and R2 disposed on opposite sides are assembled in one measurement space S1, and the reference resistors R3 and R4 disposed on opposite sides are assembled in one reference space S2, so that the thermal conductivity sensor 100 can be reduced in scale.

Also, since the Wheatstone Bridge circuit WB is constructed with the two measurement resistors R1 and R2 and the two reference resistors R3 and R4, the need for external resistors for constructing the Wheatstone Bridge circuit WB can be eliminated. Further, there is no need to consider the external temperature influence of the external resistors, thereby eliminating the need for temperature influence correction of the external resistors.

In addition, since only one reference space S2 is provided, production errors in enclosing a reference gas can be reduced. Further, the number of components can be reduced by reduction of the number of spaces, and the sensor can also contribute to reduction of the costs.

Furthermore, the detection signal can be doubled as compared with a case in which one measurement space S1 and one reference space S2 are simply provided and one measurement resistor R1 or R2 and one reference resistor R3 or R4 are provided in the spaces, so that the measurement sensitivity can be improved.

Other Modified Embodiments

Here, the present invention is not limited to the aforementioned embodiments.

For example, in the aforementioned embodiments, the sensor substrate and the lead pin 5 are connected by Au wire bonding; however, instead of that, the bonding may be implemented by Pt wire bonding. At this time, as the second layer formed on the Cr layer on one end surface of the lead pin 5, a Pt layer is formed instead of the Au layer.

Also, the connection body 6 is not limited to a wire, so that the connection body 6 may be a member having, for example, a spherical shape that intervenes between the tip end surface of the lead pin 5 and the pad portion 34.

Further, in the aforementioned embodiments, those in which a thin film resistor body is formed on a silicon substrate are used; however, it is possible to use those in which a platinum temperature-measuring resistor body is subjected to glass coating. However, in this case, variation in the structure is large as compared with the aforementioned embodiments, thereby raising a problem in that there will be variations in the measurement sensitivity. Also, since the resistor body is subjected to glass coating, the heat capacity is large, thereby raising a problem in that the response speed will be slow.

In addition, it goes without saying that a part or the whole of the embodiments and modified embodiments described above may be suitably combined, and the present invention is not limited to the aforementioned embodiments, so that various modifications can be made within a range that does not depart from the gist thereof.

What is claimed is:

1. A thermal conductivity sensor that detects a thermal conductivity of a sample gas by using a Wheatstone Bridge circuit constructed in such a manner that measurement resistors that are brought into contact with the sample gas are disposed on a first opposing side, and reference resistors that are brought into contact with a reference gas are disposed on a second opposing side, and comparing the potential difference between connection points of the reference resistors and the measurement resistors, wherein the measurement resistors disposed on the first opposing side are assembled in one measurement space in which the sample gas is housed, and the reference resistors disposed on the second opposing side are assembled in one reference space in which the reference gas is housed, wherein the measurement resistors disposed on the first opposing side are made of two thin film resistor bodies formed on one substrate surface, and the reference resistors disposed on the second opposing side are made of two thin film resistor bodies formed on one substrate surface.

2. The thermal conductivity sensor according to claim 1, wherein at least the thin film resistor bodies constituting the measurement resistors have a pattern formation part formed in a pattern on the substrate surface, and the pattern formation part has a pattern shape having a density that is highest at peripheral parts and gradually decreases toward a central part, whereby a temperature of a neighborhood of the pattern formation part can be raised to a generally uniform temperature when the pattern formation part is energized.

* * * * *